United States Patent [19]

Turre et al.

[11] 4,415,418

[45] Nov. 15, 1983

[54] GEL ELECTROPHORESIS DEVICE AND METHOD

[76] Inventors: Gilles H. J. Turre, Paris; Michel Hours, Chateaufort; Jacques R. Labrude, Palaiseau, all of France

[21] Appl. No.: 332,817

[22] Filed: Dec. 21, 1981

[30] Foreign Application Priority Data

Dec. 22, 1980 [FR] France .................... 80 27637

[51] Int. Cl.³ .................. G01N 27/26; G01N 27/28
[52] U.S. Cl. .................... 204/180 G; 204/299 R
[58] Field of Search .................. 204/299 R, 180 G

[56] References Cited

U.S. PATENT DOCUMENTS

| | | | |
|---|---|---|---|
| 2,875,144 | 2/1959 | Karler | 204/299 R |
| 3,402,118 | 9/1968 | Mutter | 204/299 R |
| 3,407,133 | 10/1968 | Oliva et al. | 204/299 R |
| 3,620,947 | 11/1971 | Allen et al. | 204/180 G |
| 4,151,065 | 4/1979 | Kaplan et al. | 204/299 R |

Primary Examiner—Howard S. Williams
Assistant Examiner—Terryence F. Chapman
Attorney, Agent, or Firm—Karl F. Ross; Herbert Dubno

[57] ABSTRACT

Horizontal gel electrophoresis is carried out in a disposable device in the form of a rectangular upwardly open tray having a pair of elongated wells at opposite ends of the container receiving the electrodes which may be insertable or can form a permanent part of the unit. A raised flat form lying below the top of the tray is disposed between the two wells and, spaced from this platform and on opposite sides thereof, removable partitions are received so that, when the gel is cast over the platform between the two partitions, the latter can be removed to allow direct contact between the two ends of the gel slab and the buffer solutions in the wells, thereby eliminating narrow bridges or other like conduct paths between the electrode-immersing buffers and the electrophoresis general body.

7 Claims, 4 Drawing Figures

GEL ELECTROPHORESIS DEVICE AND METHOD

FIELD OF THE INVENTION

Our present invention relates to an electrophoresis device and method and, more particularly, to a device for carrying out horizontal gel electrophoresis and especially to a disposable device for this purpose.

In more general terms the invention can relate to a through-type device which is preferably disposable, for effecting separation by differential migration rates and/or for studying migration in an appropriate medium, e.g. a gel.

BACKGROUND OF THE INVENTION

For many educational, laboratory, medical, research or industrial purposes, it is frequently desirable to study migration of a substance in a suitable retarding medium and/or to effect separation of complex substances by differential migration in such media.

When the driving force inducing the migration is an electric field and the medium is capable of retarding the movement of a component as a function of its molecular weight, charge and molecular size, the method is known as electrophoresis and, where separations are carried out in other ways, the methods may be various chromatographic techniques.

In all of these methods a medium is provided through which the components to be separated move at different velocities under various driving forces and with the medium being oriented differently, depending upon the purpose and the technique.

While the background of the invention will be described in connection with horizontal gel electrophoresis, therefore, it should be understood that horizontal gel electrophoresis represents the best mode currently known to us for utilizing the invention, i.e. carrying out the invention in practice. However, in its broadest sense, the invention may involve merely the study of migration of a substance in an appropriate medium or the differential separation of substances in a medium basically utilizing the same device and hence such uses are not excluded except as we have otherwise limited them in the description and the appended claims.

As noted, electrophoresis is an analytical method widely used in research and increasingly advantageous for clinical and analytical processes. While the art recognizes a variety of electrophoresis devices and methods, e.g. thin-film and column electrophoresis, the type of electrophoresis with which the invention is principally concerned can be termed horizontal gel electrophoresis.

Even in conventional systems of the latter type, complex equipment, manipulations and procedures were involved. Generally a gel was cast into slabs and the ends of each slab connected with vessels containing appropriate buffer solutions and forming conductors between the gel and the electrodes.

The electrodes are connected to opposite poles of a high voltage source, the material to be separated, with or without prior treatment, was placed upon the slab and the substances within this material migrated with different velocities, depending inter alia upon molecular weight, or at different rates under the electrical driving force applied across the slab.

The prior art devices for this purpose have been fairly complex and because of their complexity required reuse with many disadvantages. For example, the identification of the substances separated across the gel layer is usually carried out with a so-called developer having or producing a predetermined color depending upon the nature and concentration of the substance under investigation, i.e. the developer can be an indicator-type dye or forms such a dye. Even traceamounts of developers of this type present in the system may create interference with subsequent runs of a test, experiment or analysis unless the device is thoroughly cleaned since the earlier devices were not replaceable because of high cost.

Even when the unit appeared to be clean, trace amounts of the developer can create problems and hence the gel slab was frequently removed from the device prior to development simply to avoid contamination.

Because of the need to remove gel slabs for development, the gel slab had to have sufficient density so that its coherency could permit the removal. This, of course, reduced the diffusion rate for which it could be designed.

It was also necessary to form this slab with relatively large minimum thickness so that the slab could tolerate the manipulations required without deterioration.

In part because of these limitations, earlier horizontal gel electrophoresis was not fully sucessful. The manipulator steps discussed above were also found to introduce errors in the migration by surface distortion and the like and extremely precise determinations could not be made.

Washing techniques, which did not always prove to be successful for the reasons mentioned, also required a long down-time of the apparatus.

In addition, because of the requisite thickness for the gel slab and to avoid deterioration in contact with the buffer electrolyte, the bars bordering the gel slab in the region of the electrodes remained in place for the entire operation which means that communication passages were requested between the gel and the buffer. These passages create sites for the preferential passage of the electric current which caused local temperature differences interfering with the uniformity of the action. Furthermore, higher voltages were often required because of the interruption of the zones of contact between the buffer and the gel slab.

A conventional apparatus of this type is even more difficult to employ when radioactive materials are studied because the radioactivity accumulates in portions of the apparatus and can give rise to parasitic signals or noise which falsify the results. Simple disuse, of course, is impractical because the electrodes frequently are composed of a precious metal such as platinum.

Disposable trays for the gel slab have been provided heretofore in an effort to avoid some of the aforementioned problems. Such trays cooperate with an electrode tank carrying the electrodes and the buffer electrolytes and forming a unit separate from the tray. The latter tank can be placed on top of the tray with the electrolyte communicating with the gel in the tray.

This argument certainly eliminates the problems of distortion of the slab and the problems described above in connection with the handling of the slab away from the other elements of the apparatus.

Nevertheless this system was involved in a number of problems. For example for each replacement of a tray containing a slab, it is necessary to lift the electrode carrier and replace the electrode carrier. For a single reaction or run this does not create any particular difficulty but when a number of runs is required, it is necessary to provide either a multiplicity of electrode carriers or to clean the electrode carriers between each use. Furthermore, the electrode carrier, when in use for one tray, cannot be utilized for a second tray. Since the electrode carriers, tanks, etc. are complex and expensive, multiplying the number of them in a laboratory poses a significant problem. In addition, these systems do not avoid the difficulties with radioactive materials previously mentioned.

OBJECTS OF THE INVENTION

It is the principal object of the present invention to provide an improved apparatus for studying the migration of a substance or for the separation of substances in a medium whereby the disadvantages described above are obviated.

A more specific object of the invention is to provide a method of and an apparatus for horizontal gel electrophoresis whereby the problems of cleaning the apparatus are avoided.

SUMMARY OF THE INVENTION

These objects and others which will become apparent hereinafter are attained, in accordance with the present invention, in an electrophoresis apparatus which comprises an upwardly open tray of electrically insulating material, preferably comprised of a synthetic resin which is inert to the materials used, e.g. the buffer electrolytes, and provided at opposite sides with electrodes fixed in the tray and, between these electrodes, with a support surface for a gel layer.

The tray, which can be molded, especially injection molded, can make use of nonoxidizable electrodes which, however, are not composed of precious metals, e.g. electrodes of stainless steel. As a result the tray is of comparatively low cost and can be discarded after each use.

In addition, washing is no longer necessary so that a large number of analyses can be carried out simultaneously or selectively in a much shorter time than has hitherto been the case.

According to a feature of the invention the support surface is raised above wells at opposite ends of the tray which can be of rectangular shape thereby providing a rectangular platform between the wells which can be filled with the buffer electrolyte.

Between the platforms and the electrodes in these wells, we provide means for supporting movable partitions which, when inserted, can form sides of a compartment into which the gel can be cast. Upon removal of these partitions, the entire flank of the gel slab defines a wall of the well containing the electrolyte buffer and thus is in contact with the buffer over a large area while the migration of the substance takes place in the layer of gel by lowering the platform so that this gel layer can be of small thickness and of low density, thereby permitting high diffusion rates to be sustained without the danger of distortion.

Obviously, it is possible to apply the developer or indicator without removing the gel from its support, thereby greatly facilitating the precision of measurement of the diffusion distances.

The bars hitherto considered to be necessary between the wicks or bridges and the buffer are eliminated and local voltage and temperature differences are excluded.

Furthermore, the upper surface of the platform can be engraved or otherwise marked with a grid or other indicia facilitating measurement of the migration distances, the walls of the tray can be provided with supports for an insulating but transparent cover which can be put in place during the application of the voltage, or the device can be supplied with a comb or the like for indenting recesses in the gel to receive the samples.

The device provides many other advantages some of which will be discussed below, but apart from the fact that it is disposable, it also permits preparation of a large number of gels in respective trays utilizing automatic gel distributors of the type used to produce a large number of cultures in Petri dishes etc. The electrolyte buffers can also be introduced into the automatically prepared trays by automatic metering means.

BRIEF DESCRIPTION OF THE DRAWINGS

The above and other objects, features and advantages of the present invention will become more readily apparent from the following description, reference being made to the accompanying drawing in which.

SPECIFIC DESCRIPTION

Figure 1:
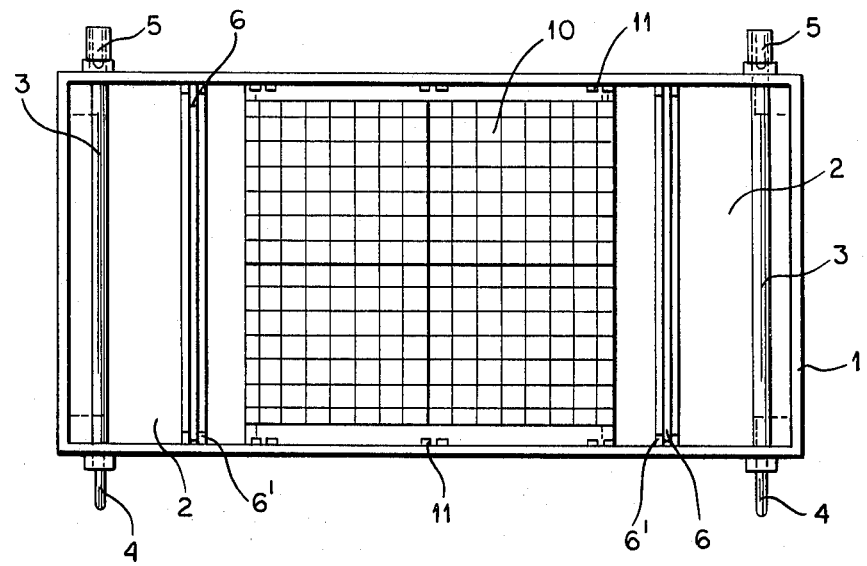
FIG. 1 is a diagrammatic plan view of a horizontal gel electrophoresis device in accordance with the present invention.

In the drawing we have shown a tray 1 which is injection molded from a transparent synthetic resin material such as polystyrene which is electrically insulating and is inert to the electrolyte buffers utilized in electrophoresis. Naturally other materials with the same properties and which may not be transported can also be used, the material being primarily selected with the experimental need, e.g. for transparency to ultraviolet radiation, for thermal resistance permitting autoclave sterilization and/or for resistance to various chemical agents which may be employed.

Tray 1 is of parallelopipedal configuration preferably rectangular as shown, of a small thickness or depth so that at each end a wall 2 is formed in which the electrode 3, extending at full width of the tray, is received, the electrode 3 being sealed to the opposite longitudional walls thereof.

The electrode 3 are nonoxidizable metal rods or rods which have received a nonoxidizable conductive coating by a surface treatment or covering. Preferably neither the bars nor the surface is formed from a precious metal.

Each end of each electrode passes through the longitudinal wall in which it is sealed. One of the projecting ends can form a male electrical connector or plug 4 which mates with a jack or female electrical connector such as has been shown at 5 at the opposite projecting end of each electrode. It will be apparent, therefore, that a number of such trays can be assembled side by side with the plugs of one tray being electrically connected at and receivable within the jacks of the next so that the source of high voltage need only be connected to the electrode at one end of the assembly to service the entire array.

The number of trays used is limited only by the electric power availability and this arrangement permits a large number of tests to be made simultaneously although the systems can operate with only a single tray.

The walls 2 are adapted to receive the usual electrolyte buffers in which the electrodes 3 are immersed.

At the center of the tray, there is a raised platform 9 which is preferably square and has dimensions of 10 cm×10 cm and provided with an etched, engraved, embossed or printed grid surface 9', calibrated preferably in milimeters, and visible through the gel 10 which is utilized.

Any conventional electrophoresis gel can be employed although agar or acrylamide gels are preferred.

Figure 2:
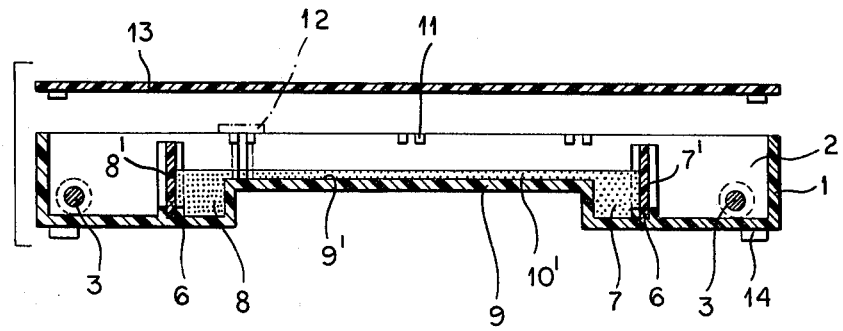
FIG. 2 is a cross sectional view through this apparatus showing the cover spaced thereabove.

Between the platform 9 and the electrodes 3, the tray along its bottom and longitudinal walls is formed with ribs 6' defining a groove into which partitions 6 can be inserted. As can be seen from FIG. 2, when the partitions 6 are in place hot gel 10 can be poured onto the platform 9 so that the gel forms a thin layer 10' over this platform, and thick bodies 7 and 8 on either side of the platform.

When the partitions 6 are removed, the end surfaces 7' and 8', of the bodies 7 and 8 which act as wicks, connect the electrolyte buffer. Naturally, the partitions 6 are only removed once the gel has cooled so as to be self supporting.

Figure 4:
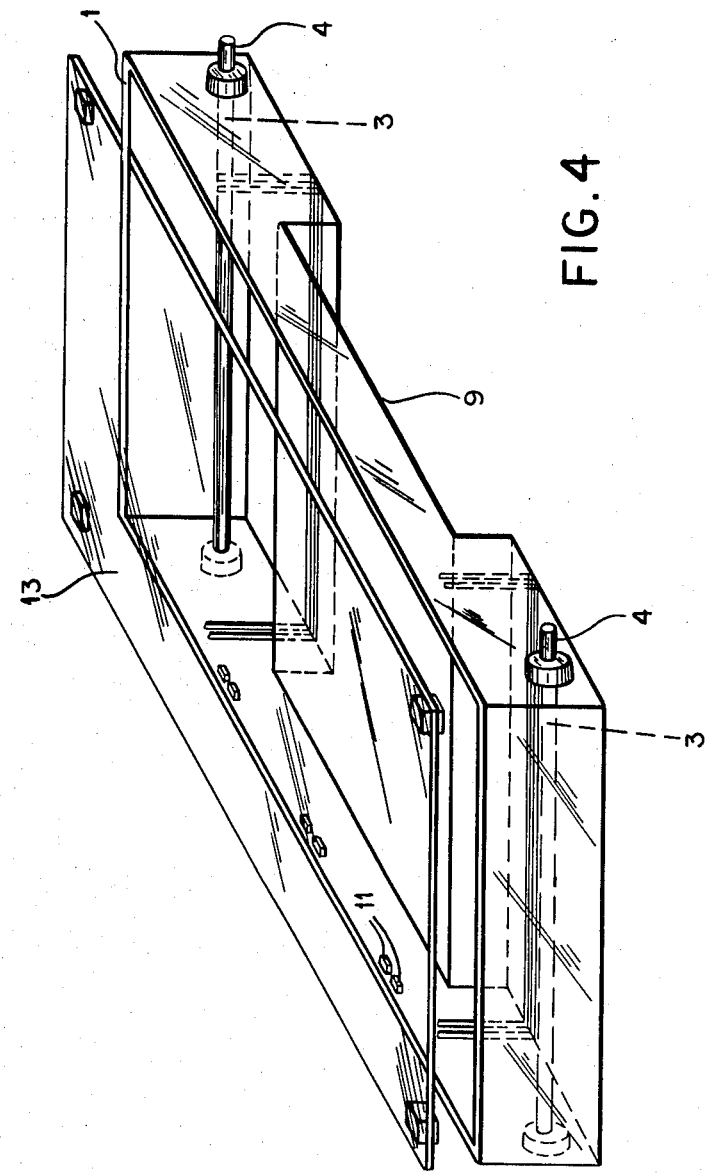
FIG. 4 is a perspective view of the apparatus.

A cover 13 (FIGS. 2 and 4) is provided to close the tray, limit evaporation and form a shield against inadverted electrical contact by the experimenter.

Figure 3:
FIG. 3 is a perspective view of a comb which can be used with the apparatus of FIG. 2.

The longitudinal walls of the tray 1 are formed with lugs 11 into which the blade 12' of a comb 12 can be inserted (see FIGS. 2 and 3) so that the fingers of the comb penetrate into the gel layer and, as it is cooling, form sample-receiving cavities thereof.

Bosses or feet 14 can be formed on the underside of the tray and are set inwardly so that they can enter an underlying open tray for stacking of the trays, each foot 14 being received at a corner of the underlying tray. The stacked trays may be empty or full.

In use for slab electrophoresis the trays are prepared and sterilized in the manner described, the samples placed in the cavities formed in the gel and the high voltage electrophoresis current is applied. If desired, the tray can be exposed to ultraviolet light to which it is transparent for fluorescent indication of the relative migrations. Furthermore, to avoid distortion by meniscus effects, the grid 9' is spaced inwardly of the longitudinal sides of the tray.

The trays can be manufactured at low cost and hence can be discarded after use. Because the slab is not handled apart from the tray, distortion is excluded and extremely precise readings of migration distances can be obtained. Only small quantities of gel and buffer electrolyte are required.

Furthermore, experimental conditions can readily be standardized by the use of mass produced trays and it is possible to carry out electrophoresis in a large number of trays simultaneously thereby reducing the time required for this work. In fact, by assembling groups of trays, each group can be connected to a different voltage source or all of the trays can be connected together for operation by a single source without difficulty.

The apparatus is safe to use, since the experimenter is not required to handle directly toxic or radioactive products, especially since there is no need to remove the gel for handling and washing, of course, is completely eliminated.

Since the contact between buffer electrolyte and gel occurs over a wide area without interruption, lower voltage sources are required that has hitherto been the case.

The invention can be used for immunological research by electrophoresis, e.g. for the analysis of antigens and antibodies (immune electrophoresis), for the analysis of proteins and nucleic acids and for investigations with toxic and radioactive products in addition to the other gel separation and preparative gel research well known in the art.

The trays can be prepared in advance, stored and used as required.

We claim:

1. An apparatus for effecting migration of a substance in a gel medium by horizontal gel electrophoresis which comprises:
   an upwardly open tray formed with a support surface for said gel medium;
   a pair of electrodes fixed in said tray on opposite sides of said support surface; and
   a pair of removable partitions received in said tray between said electrodes and said support surfaces whereby said medium, originally confined by said partitions, directly contacts an electrolyte in which each of said electrodes is immersed upon removal of said partitions, said support surface being formed as a platform in said tray between wells for said electrolyte and receiving said electrodes, said support being provided with a grid visible through said gel medium and inset from opposite walls of said tray whereby migration distances can be readily read from said grid, said electrodes being formed at least along their surface in contact with said electrode of a nonoxidizable nonprecious metal, each of said electrodes having an end passing through one of said walls and formed with a male plug for electrical connection, the other end of each electrode passing through the opposite wall of said tray and being formed with a female jack adapted to receive a corresponding plug of another similar tray whereby said trays can be assembled in side-by-side relationship and electrically connected.

2. The apparatus defined in claim 1 wherein said tray is molded in a single piece of synthetic resin material transparent at least to ultraviolet light, stable at sterilizing temperatures and chemically inert under the conditions of use, said apparatus further comprising a cover adapted to fit on said tray.

3. The apparatus defined in claim 1 wherein said walls are formed with lugs adapted to guide a comb so that its fingers penetrate into said gel and on the cooling thereof form sample receiving recesses.

4. A method of gel electrophoresis, comprises:
   (a) preparing a plurality of gel electrophoresis trays by casting an electrophoresis gel over a plate formed between a pair of movable partitions separating the plate from electrodes permanently fixed in each tray, cooling the gel, removing the partitions, and introducing a buffer electrolyte between a flank of the cooled gel and a respective electrode;
   (b) assemblying the plurality of trays prepared as in step (a) by plugging outwardly extending formations of electrodes of one tray into sockets connected to the electrodes of an adjacent tray;
   (c) placing samples on said gels of said trays;
   (d) applying an electrophoresis voltage across the electrodes of the assembled trays to cause migration of said substances on the gels of said trays;

(e) determining the degree of migration of samples on said trays; and (f) discarding said trays.

5. A disposable gel electrophoresis apparatus comprising:

an upwardly open tray formed integrally in one piece and with all thicknesses being the same, said tray having:

a pair of opposite end walls, a pair of opposite longitudinal walls adjoining said end walls, and a floor surrounded by said walls, said floor defining a centrally located raised gel-receiving platform and a pair of lower floor portions between said platform and said end walls respectively;

a pair of removable partitions each received in said tray between said platform and a respective one of said end walls and subdividing the respective lower floor portion into a gel-receiving space adjacent said platform and an electrolyte-receiving space between the partition and the respective end wall;

a pair of electrodes each spanning said longitudinal walls in the respective electrolyte-receiving space whereby electrolyte in said electrolyte-receiving space is in direct contact with the respective electrode and a slab of said gel over the entire height and width of said gel-receiving space upon the removal of the respective partition; and a lid fitting onto said tray.

6. The apparatus defined in claim 5 wherein each of said electrodes externally of said tray and adjacent one of said longitudinal walls a respective plug fitting and externally of said tray on the opposite longitudinal wall a respective jack fitting, said plug and jack fittings being interconnectable whereby said tray may be connected electrically with similar trays in a side-by-side assembly for energization in parallel from a common source.

7. The apparatus defined in claim 5 wherein said platform is a support surface visible through said gel and engraved with a graduated measuring grid allowing measurement of migration distances without removal of the gel from the tray.

* * * * *